United States Patent [19]

Ripp

[11] Patent Number: 5,124,126
[45] Date of Patent: Jun. 23, 1992

[54] MEDICAL/DENTAL OFFICE WASTE DISPOSAL

[76] Inventor: Gerard A. Ripp, 406 Fulton St., Troy, N.Y. 12180

[21] Appl. No.: 699,907

[22] Filed: May 14, 1991

Related U.S. Application Data

[63] Continuation-in-part of Ser. No. 301,508, Jan. 24, 1989, abandoned.

[51] Int. Cl.$^5$ .......................... A61L 2/00; B03B 9/06; B02C 19/12
[52] U.S. Cl. .......................... 422/26; 422/1; 422/292; 422/300; 100/122; 100/131; 100/229 A; 241/99; 220/908
[58] Field of Search .............. 422/1, 26, 294, 295, 422/292, 300; 53/527, 529; 428/2; 241/99, DIG. 38; 100/122, 131, 229 A; 220/908

[56] References Cited

U.S. PATENT DOCUMENTS

| | | | |
|---|---|---|---|
| 3,185,339 | 5/1965 | Fleming | 220/98 |
| 3,451,185 | 6/1969 | Tezuka | 428/2 |
| 3,633,329 | 1/1972 | Nadler | 100/229 A |
| 4,105,412 | 8/1978 | Petzinger | 210/67 |
| 4,303,412 | 12/1981 | Baikoff | 428/2 |
| 4,374,491 | 2/1983 | Stortroen et al. | 100/73 |
| 4,552,720 | 11/1985 | Baker, Sr. et al. | 422/26 |
| 4,670,227 | 6/1987 | Smith | 422/297 |
| 4,680,808 | 7/1987 | Paleschuck | 383/9 |

*Primary Examiner*—Robert J. Warden
*Assistant Examiner*—Theresa A. Trembley
*Attorney, Agent, or Firm*—Morgan & Finnegan

[57] ABSTRACT

A method and apparatus for the disposal of solid and liquid medical waste that is to be ultimately autoclaved prior to final disposal, to be used in conjunction with existing equipment already present in medical facilities. The device provides an apparatus capable of collecting solid medical waste while permitting the exit of liquid medical waste. An outer shell includes removable porous holding apparatus inserted therein for holding and compacting solid waste for subsequent autoclaving, while simultaneously permitting the exit of liquid waste into a separate collection vessel for subsequent autoclaving. Alternatively, a porous inner shell is placed within an outer shell to define a drainage chamber, for draining liquid waste separated from the solid waste that is introduced into the inner chamber, so that the liquid medical waste may be externally collected for autoclaving. The solid waste is compacted within the inner chamber and released from the device, via an integral mechanism, for collection in an external cannister prior to autoclaving.

11 Claims, 6 Drawing Sheets

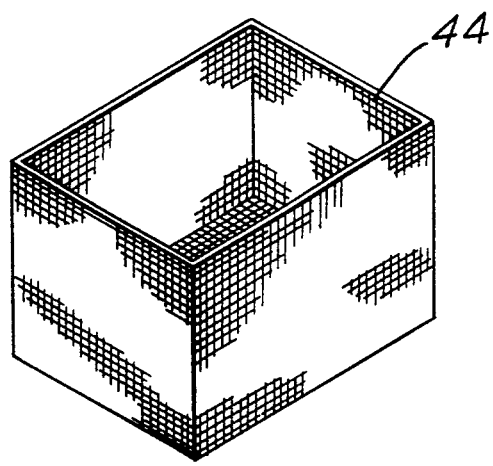
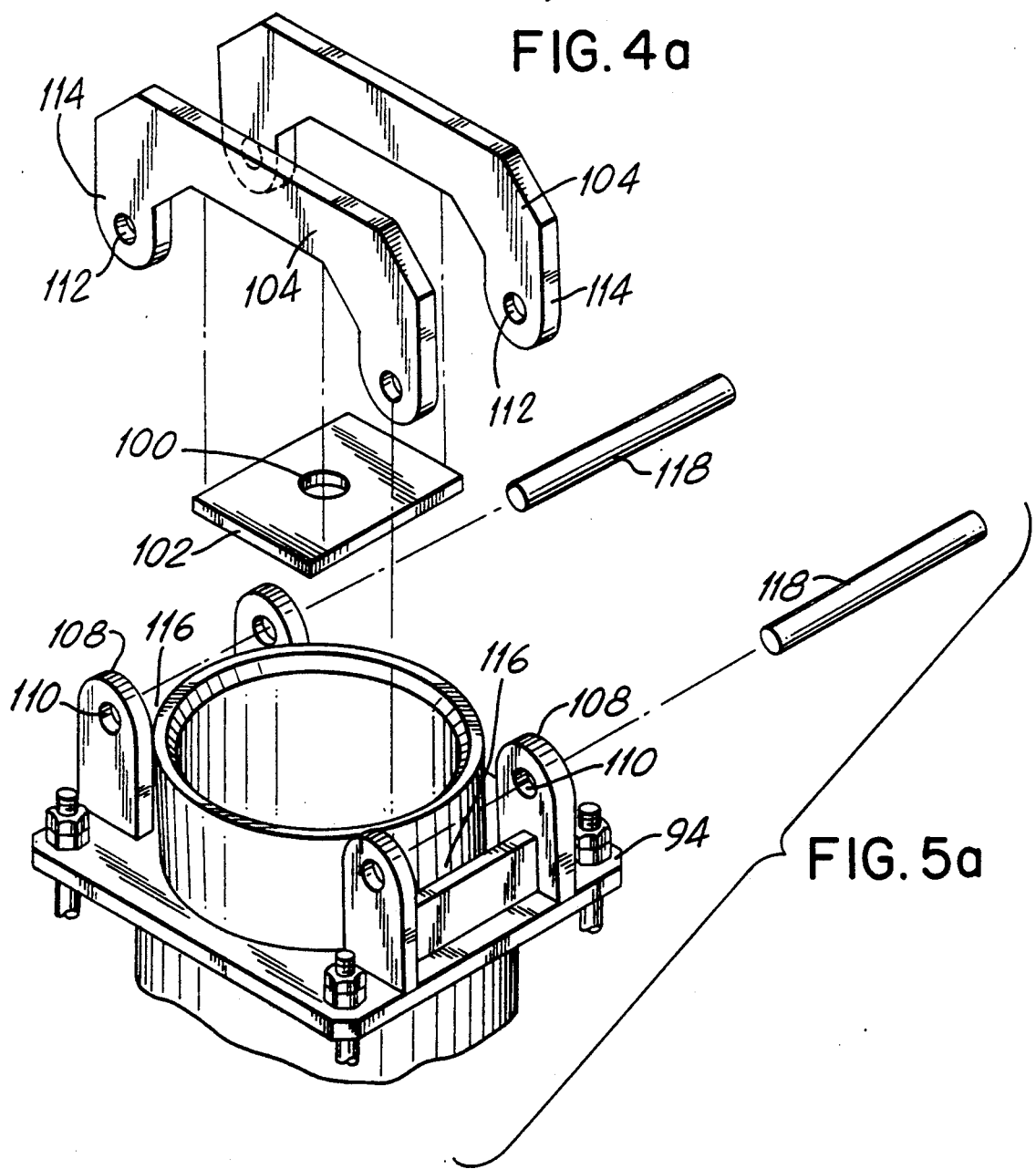

MEDICAL/DENTAL OFFICE WASTE DISPOSAL

CROSS-REFERENCE TO RELATED APPLICATIONS

This is a continuation-in-part of co-pending application Ser. No. 07/301,508, filed on Jan. 24, 1989.

TECHNICAL FIELD OF THE INVENTION

The present invention relates to a method and apparatus for collecting solid and liquid wastes for autoclaving prior to disposal, and more particularly, for the safe collection, separation, and subsequent autoclaving prior to disposal of hazardous solid and liquid waste generated in medical offices.

BACKGROUND AND OBJECTS OF THE INVENTION

The field of medical waste disposal is one looked at with great concern in today's environment. There is an increasing dichotomy between the need to bring effective, efficient and widespread medical attention to everyone, and the immense amount of volatile and hazardous waste generated by such widespread medical attention.

Medical attention is typically done in small selfcontained doctor's offices and clinics. In order to operate effectively, these offices and clinics must exist on a limited budget and use devices of limited complexity.

The known methods and devices used for medical waste disposal, however, are both complex and expensive. They also must be used in conjunction with special knowledge and equipment rendering them impractical for a small medical practitioner.

One such known device can be seen in U.S. Pat. No. 4,552,720, by Baker, Sr., et al. for "Debris Compressing Autoclave." The device shown in Baker is very complex (shown therein in FIG. 6), and requires a specially designed thermoplastic liner (shown therein in FIGS. 2 and 8).

The Baker apparatus has a built-in autoclave. Once the waste is introduced into the device, the device is sealed and the waste is autoclaved. After autoclaving, while the waste is still hot, the apparatus compacts the waste and thereby causes the thermoplastic liner to deform around the waste. This procedure limits the Baker apparatus to only one compaction per waste disposal cycle, and thereby limits the amount of waste the apparatus may handle.

The Baker apparatus is extremely complex, cost inefficient, requires special supplies and know how, and handles a low quantity of waste per disposal cycle. It is therefor unsuitable for the limited use a doctor's office may require.

A second such known device is described in U.S. Pat. No. 4,374,491, by Stortroen et al., for "Apparatus for Treating and Disposing of Bio-Hazardous Waste and Solid Waste." The Stortroen apparatus uses a complex set of chambers and pistons to autoclave waste and then move the waste around throughout the apparatus and into storage. The Stortroen apparatus requires a special "compactor storage device" (shown therein by numeral 41, in FIG. 2) for storage of the waste product and transportation to final disposal. This complexity and special storage apparatus makes the Stortroen device also unsuitable for usage in a doctor's office.

The inadequacies of these known medical waste disposals leaves individual medical practitioners with the choice of "red-bagging" hazardous waste in a special container for disposal purposes. "Red-bagging" requires special handling for disposal purposes because the waste is not sterilized or compacted in the doctor's office. "Red-bagging" has proven to be an unsatisfying method which is extremely harmful to the environment.

It is therefor an object of the present invention to provide a method and apparatus for the inexpensive, simple and safe disposal of solid and liquid medical waste for subsequent autoclaving prior to disposal.

It is a further object of the present invention to provide a method and apparatus for the disposal of solid and liquid medical waste which may be simply adapted to a doctor's office.

It is still a further object of the present invention to provide a method and apparatus for the disposal of solid and liquid medical waste which does not require using special equipment not already available in a doctor's office.

It is still a further object of the present invention to provide a method and apparatus for the disposal of solid and liquid medical waste which does not require any special knowledge to use.

Still further objects of the invention may be simply revealed to one skilled in the art through the following description of the invention and its embodiments.

SUMMARY OF THE INVENTION

The present invention relates to a method and apparatus for disposing of solid and liquid medical waste. The device permits the separation of solid waste from the liquid waste, so that the collection of solid waste is permitted while allowing liquids to exit the device for external collection.

In one embodiment of the apparatus according to the invention, the device has an outer spatter shell with a perforated base. An inner chamber for collecting the solid waste, while permitting the exit of the liquid, is fitted inside the shell. This inner chamber is perforated and lipped at the top. The inner chamber catches the waste (see FIG. 2(a)) and permits liquids to drain into a liquid collector.

The lipped top may be removable, giving easy access to the inner chamber. The liquid collector may also be removed (see FIG. 2(c)) and separately autoclaved with the liquids inside, or the liquids may be drained into a separate vessel from a liquid collector which is stationary. If the liquids are drained out of the collector, then they are fed into a second container, where they may then be transported to an autoclave for autoclaving.

A disposable gauze bag may line the inner chamber, and a compactor or plunger fits into the lined inner chamber to compact the waste (see FIG. 2(b)). Since the gauze bag retains its shape, the compactor may compact the waste many times prior to producing a final waste product. This enables the present invention to accept a great amount of waste per disposal cycle, and thereby increases the waste load phenomenally.

When the waste is compacted, the gauze bag is bound around the compacted waste in such a way as to form a gauze enveloped brick 21 (see FIG. 2(c)), which may then be easily transported to an autoclave for sterilization.

In another embodiment according to the invention, the gauze liner is eliminated. A wire mesh container, or other similar rigid, porous insert, may be placed within the inner, perforated chamber. The rigid insert permits the collection of solid waste, while the liquids are allowed to drain through the mesh container and inner chamber for collection by the liquid collector. The mesh container, when filled to a desired amount with compacted waste, may simply be lifted from the apparatus for autoclaving.

In a modification of the above-described embodiment, the wire mesh container would eliminate the need for the inner perforated chamber. In this arrangement, the mesh container is placed directly within the outer spatter shell, such that the bottom of the mesh container rests upon the perforated base of the spatter shell. Solids will be collected in the mesh container, while liquids will drain through the perforated base of the spatter shell for collection by the liquid container. Thus, the apparatus may be greatly simplified and reduced in cost.

Still another embodiment according to the invention eliminates use of a removable gauze liner or removable rigid inner container to facilitate the disposal of solid waste. In this embodiment, a perforated inner chamber is affixed within the confines of an outside container chamber. The chambers are dimensioned such that a drainage chamber for draining liquids is formed between the inner surface of the outside chamber, and the outer surface of the inner, perforated chamber. Waste introduced into the inner chamber is compacted via a plunger mechanism. A drainage pipe is placed in communication with the drainage chamber and extends through the outside chamber, so that the liquids which are compacted from the solid waste can be separated and drained from the inner container and into an external collection vessel.

Both the inner and outer chambers may be substantially bottomless. The chambers are supported at their lower ends by a horizontal plate, which plate has an opening substantially conforming to the interior dimensions of the inner, perforated chamber. An extensible drawer is integrally built into the bottom plate and substantially conforms to the dimensions of the plate opening.

When in the closed, retracted, position, the drawer covers the opening so as to form a closed bottom surface for the inner chamber, such that waste material introduced into the disposal is compacted against it. When the drawer is slid outwards, the plate opening is uncovered, so that the bottomless inner chamber may release the compacted waste mass through the opening and into a collection vessel placed below the inner chamber/outer chamber arrangement. The solid waste may then be conveniently autoclaved for disposal.

Autoclaves are already regularly present in medical facilities, and therefor no additional special equipment is required. Once the waste has been autoclaved, it may then be simply discarded without requiring special handling or storage devices.

The present invention seems to be particularly suited for use in medical offices because of its small size, simplicity of operation, ability to handle large amounts of waste, an ability to operate in conjunction with existing autoclaves. The present invention therefor provides a ready method and an inexpensive apparatus for disposing of medical waste.

BRIEF DESCRIPTION OF THE DRAWINGS

The invention will now be described in greater detail below by way of reference to the following drawings, in which:

FIG. 4(a) is a perspective view of the rigid, porous container employed with the embodiments of FIGS. 3 and 4;

FIG. 5(a) is an exploded perspective view of the top portion of the embodiment of FIG. 5;

DETAILED DESCRIPTION OF THE INVENTION

Figure 1:
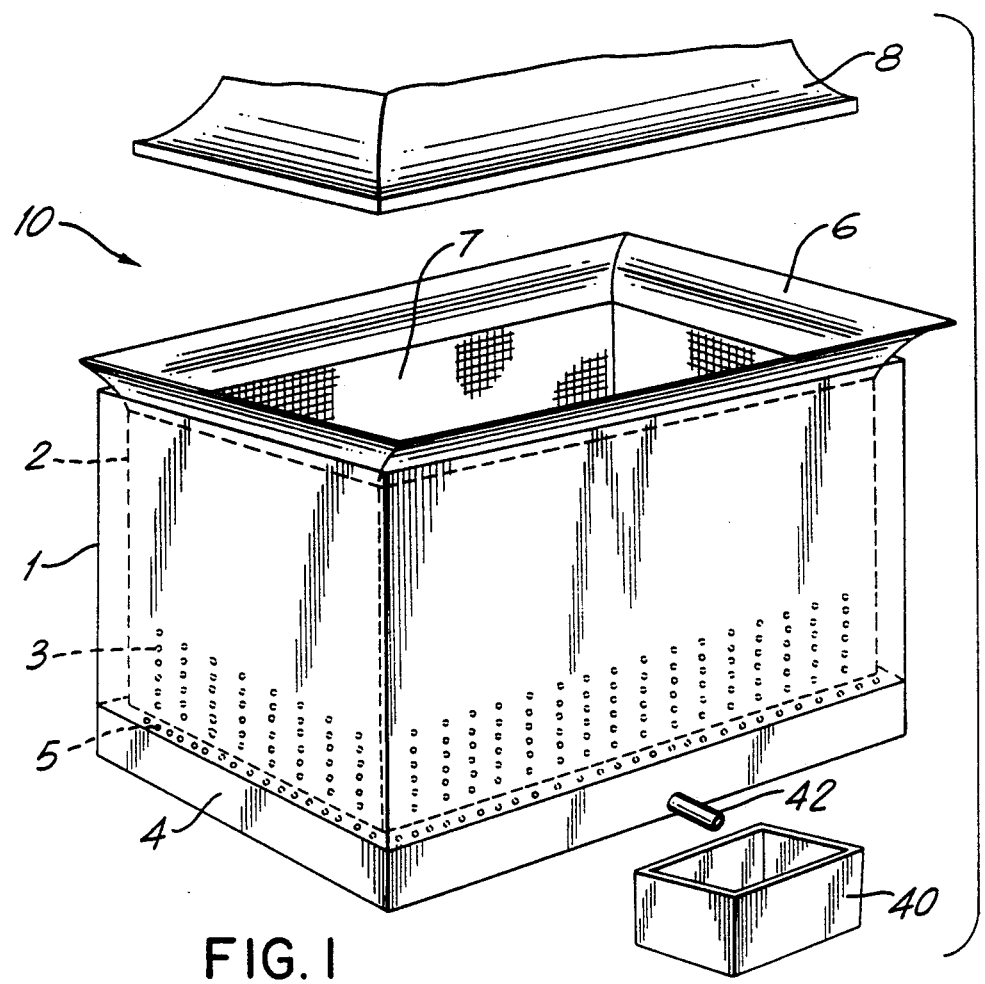
FIG. 1 is a plan view drawing according to one embodiment of the present invention.
Figure 2A:
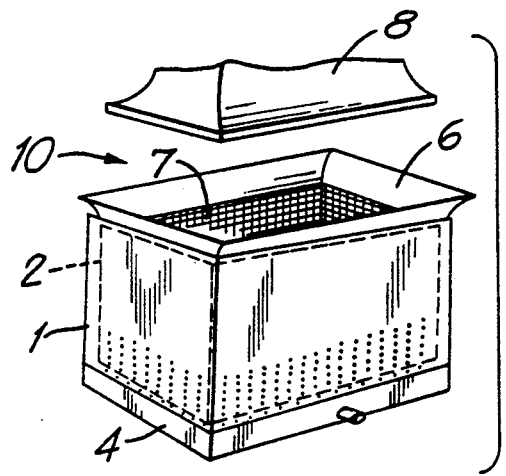
FIG. 2(a) is an explanatory drawing of waste being introduced to the embodiment of FIG. 1 of the present invention.

FIGS. 1 and 2 illustrate one preferred embodiment of the present invention. Referring to FIG. 1, numeral 1 denotes an outer spatter shell which has a perforated base 5. The shell 1 is shaped and sized in such a way as to allow an inner chamber 2 to be fitted inside. The inner chamber 2 has a lipped top 6 which allows the disposal device 10 to catch waste being introduced. (See FIG. 2(a)). This lipped top 6 may be removable to allow easy access to the inner chamber. 2.

Figure 2B:
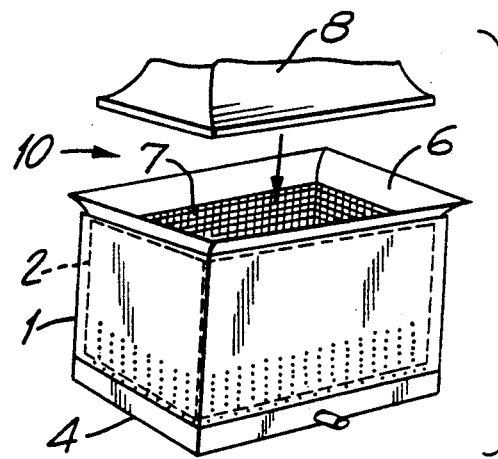
FIG. 2(b) is an explanatory drawing of the compaction of waste, and the flow of liquids, in the embodiment of FIG. 1 of the present invention.
Figure 2C:
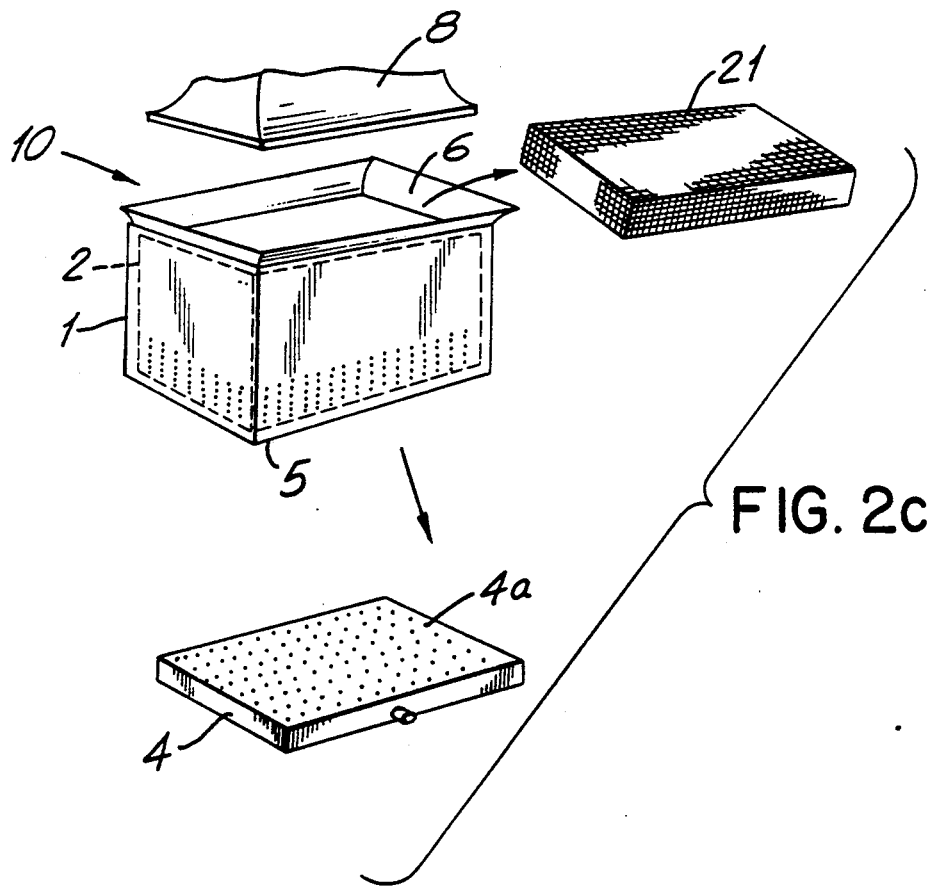
FIG. 2(c) is an explanatory drawing of the removal of the waste product, and the liquids, for autoclaving (not shown) in the embodiment of FIG. 1 of the present invention.

The inner chamber 2 also has a perforated bottom 3. This permits liquids to drain through the perforations 3 into a chamber surrounded by the outer spatter shell 1. The liquids then flow through the spatter shell's perforated base 5 and into a liquid collector 4. As shown in FIG. 2c, this liquid collector 4 may comprise, for example, an enclosed box having a perforated top portion 4a in communication with the perforated bottom 5 of the outer spatter shell 1. The liquid collector 4 may be detachably affixed to the disposal device 10, employing means well known to those skilled in the art, so that the collector 4 may be removed from the disposal device 10 for autoclaving. Also, when the collector 4 is affixed to the disposal device 10, a water-tight seal may be produced between the perforated base 5 of the spatter shell 1 and the perforated top 4a of the collector 4, employing, for example, (not shown) gaskets or sealants, employed around the periphery of the interface created by the base 5 and perforated top portion 4a, or precision of fit, or other means well known to those skilled in the art. This seal advantageously prevents the leakage of liquids from the disposal device 10.

Numeral 7 denotes a flexible porous material, such as a gauze liner, but not so limited, which fits inside the inner chamber 2. The gauze liner 7 lines the inner chamber 2 and acts as a disposable bag for packaging the final waste product during disposal.

Numeral 8 denotes a compaction device. The compactor 8 substantially conforms to the inner dimensions of and fits inside the gauze lined inner chamber 1, and mechanically compacts the waste that has been introduced therein. This is illustrated in FIG. 2(b). The compactor 8 may be driven downward under either a mechanical or human force. Compaction may be repeated a number of times as new waste is introduced into the inner chamber 2, allowing a great amount of waste to be compacted into a small waste product.

Referring to FIG. 2(c), numeral 21 denotes a gauze wrapped waste brick. This brick 21 has resulted from the compaction shown in FIG. 2(b). The waste is wrapped in the gauze liner 7 which ha been folded down and bound producing a transportable brick 21. In addition to acting as a transportable container for the final waste product, the easy flow through of the gauze allows the entire package to be simply placed in an autoclave. The brick 21 is then autoclaved in an autoclave device (not shown), which is known and utilized throughout the medical profession. After autoclaving, the wrapped, sterilized brick may then be safely and easily disposed of.

The liquids which have drained out of the waste and into the liquid collector 4 may then be disposed of in one of several manners. As previously explained, since the collector 4 is detachable from the disposal device 10, the liquid collector 4 may be removed (shown in figure (c)) and separately autoclaved with the liquid contained therein. Alternatively, the liquids may be drained into a second container 40. For example, liquids may be drained via a nozzle or tube 42 placed in communication with the interior of the collector 4, and this second container may be autoclaved. Once the liquids have been autoclaved, they too may be simply disposed of. Accordingly, it is well seen how solid wastes are separated from the liquids, so that the solids are collected for autoclaving, while the liquids are allowed to exit from the disposal for external collection, or for collection by the affixed liquid collector; prior to the autoclaving procedure.

Another embodied apparatus might be thought to be cylindrical in shape, instead of the rectangular shape of the embodiment disclosed in FIG. 1.

Figure 3:
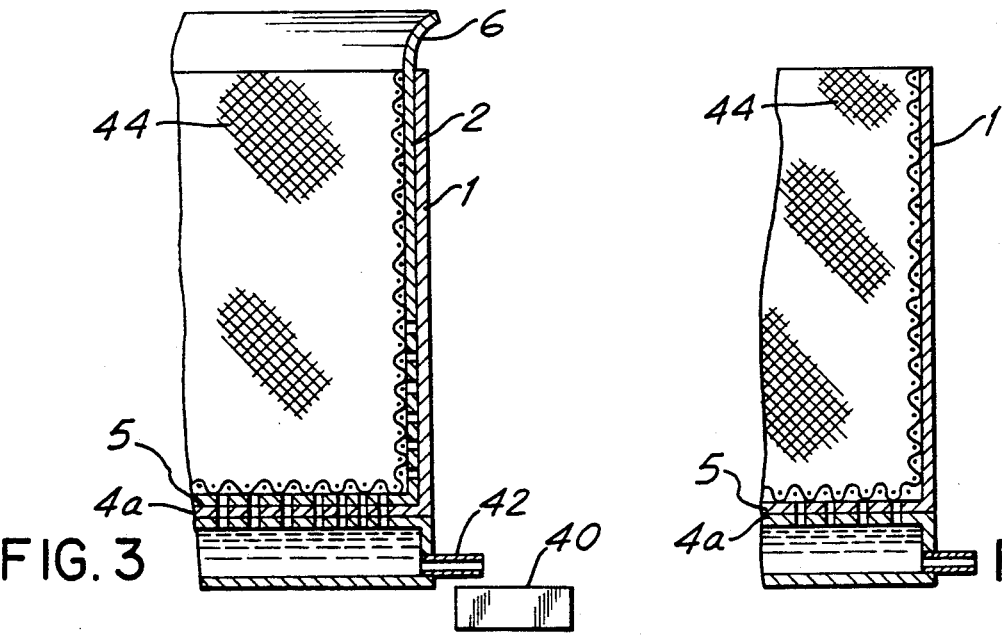
FIG. 3 is a plan view of a further embodiment according to the invention showing the elimination of the inner gauze liner in favor of a rigid, porous container.
Figure 4:
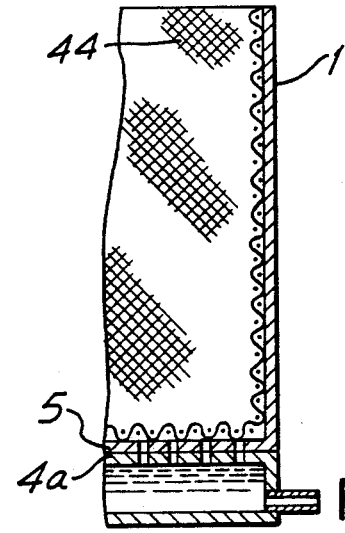
FIG. 4 is another plan view of a further embodiment according to the invention, wherein the inner perforated chamber and gauze liner are eliminated in favor of a rigid porous container.

FIGS. 3, 4, and 4(a) are directed to other embodiments according to the invention. Here, a rigid porous container 44, which may be formed in the configuration of a wire mesh cage (see FIG. 4a), but is not so limited, replaces the gauze liner 7. As shown in FIG. 3, the porous container 44, which is removable from the disposal device 10, is configured to fit snugly within the interior of the inner chamber 2. As waste is introduced into the porous container 44, liquids will be allowed to drain through the porous container 44, through the inner perforated chamber 2 and through the perforated base 5 of spatter shell 1, for collection by the liquid collector 4. Alternately, as discussed with reference to the embodiment of FIGS. 1 and 2(a)-(c), and as seen in FIG. 3, liquids may be collected into a second container 40. Here, a nozzle or tube 42 or similar arrangement may be placed in communication with the interior of the liquid collector 4, such that liquids which drain through the porous container 44 and through the inner chamber 2 may be collected in the second vessel 40 for autoclaving.

Alternatively, as seen in FIG. 4, the porous container 44 may replace both the gauze liner 7 and the inner perforated chamber 2, so that the porous container 44 is placed directly within the outer spatter shell 1. Liquids drain through the porous container 44 and through the perforated base 5 of the spatter shell 1, allowing liquids to drain into the collector 4 for autoclaving. Advantageously, as previously described, a nozzle or tube 42 may be placed in direct communication with the interior of collector 4 so that the liquids may be drained into a separate vessel for autoclaving.

In each of the embodiments shown in FIGS. 3 and 4, once the porous container 44 has been filled with compacted waste material, the container may be conveniently lifted from the disposal 10 via mechanical or human means. The filled container 44 may then be autoclaved together with the waste material therein. Once autoclaved, the sterilized waste material may be removed from the container 44 for safe disposal.

Another embodiment according to the invention is disclosed in FIGS. 5-9. Here, as previously described the solid waste material is collected and compacted, while the liquid is separated from the solid and drained from the disposal device into a separate vessel 40 for autoclaving. However, the solid compacted waste is not lifted out from the disposal; rather, the solid compacted waste is released from the disposal device through the bottom of an inner perforated chamber 46 into a separate collection cannister 48 for autoclaving. Thus, individual waste vessels are employed for collecting the liquid and solid, respectively, for autoclaving.

Figure 5:
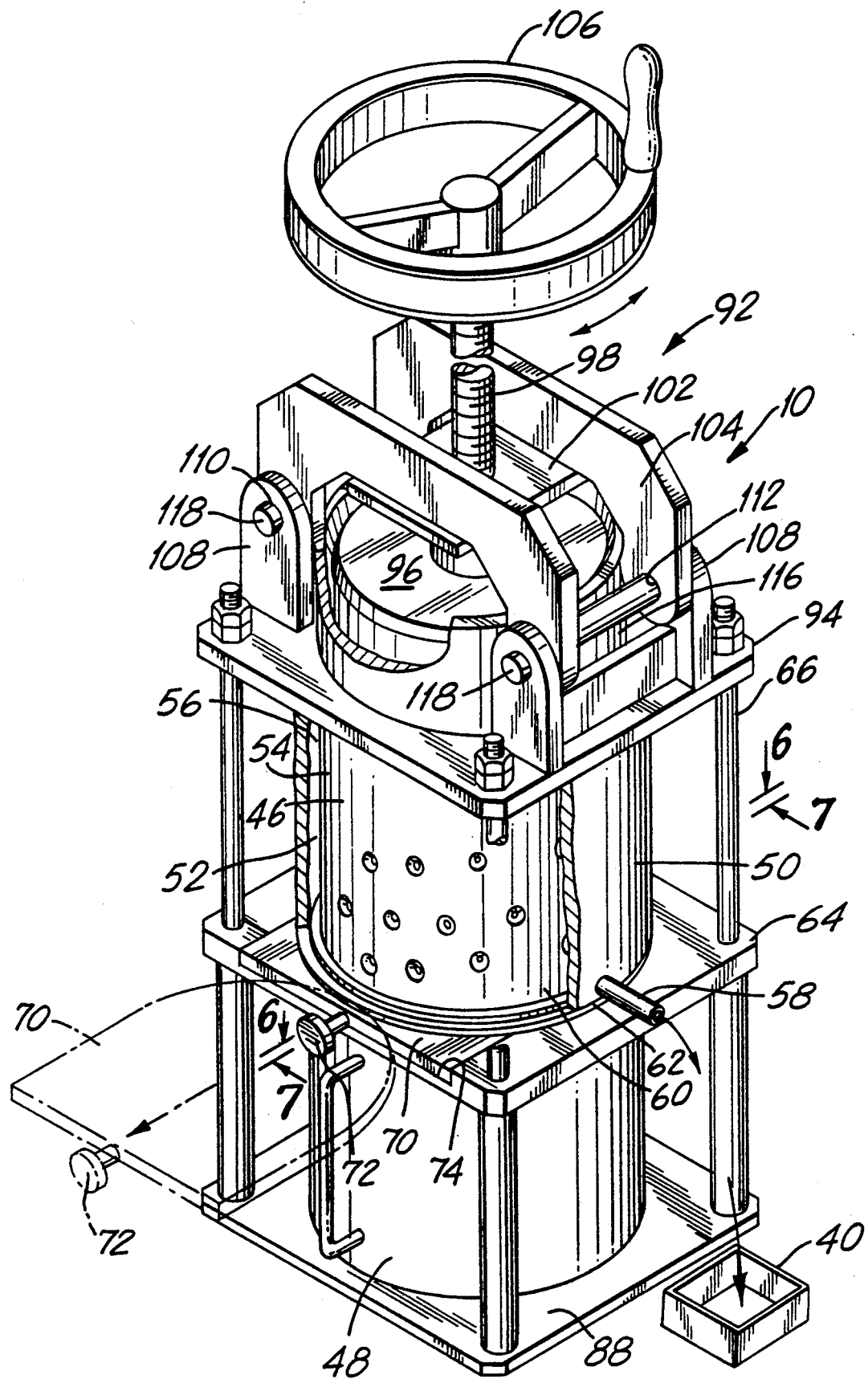
FIG. 5 is a plan view according to another embodiment according to the invention, wherein the compacted waste is emitted through a drawer from the inner chamber into a collection vessel.

Referring to FIG. 5, the disposal device 10 comprises a perforated inner chamber 46 placed within the confines of an outer chamber 50, such that a drainage chamber 52 is defined, around the periphery of the disposal device 10, between the outer surface 54 of the inner chamber and the inner surface 56 of the outer chamber. The inner chamber 46 and outer chamber 50 may be formed, for example, from portions of cylindrical tubing or the like, such that the chambers 46, 50 will be substantially hollow and will be open at their top ends and at their bottom ends. Advantageously, as also seen in FIG. 8, a pipe or nozzle 58 is placed in communication with the drainage chamber 52 and passes through the outer chamber 50 for the expulsion of liquids from the disposal 10 into a separate vessel 40 for autoclaving.

Figure 6:
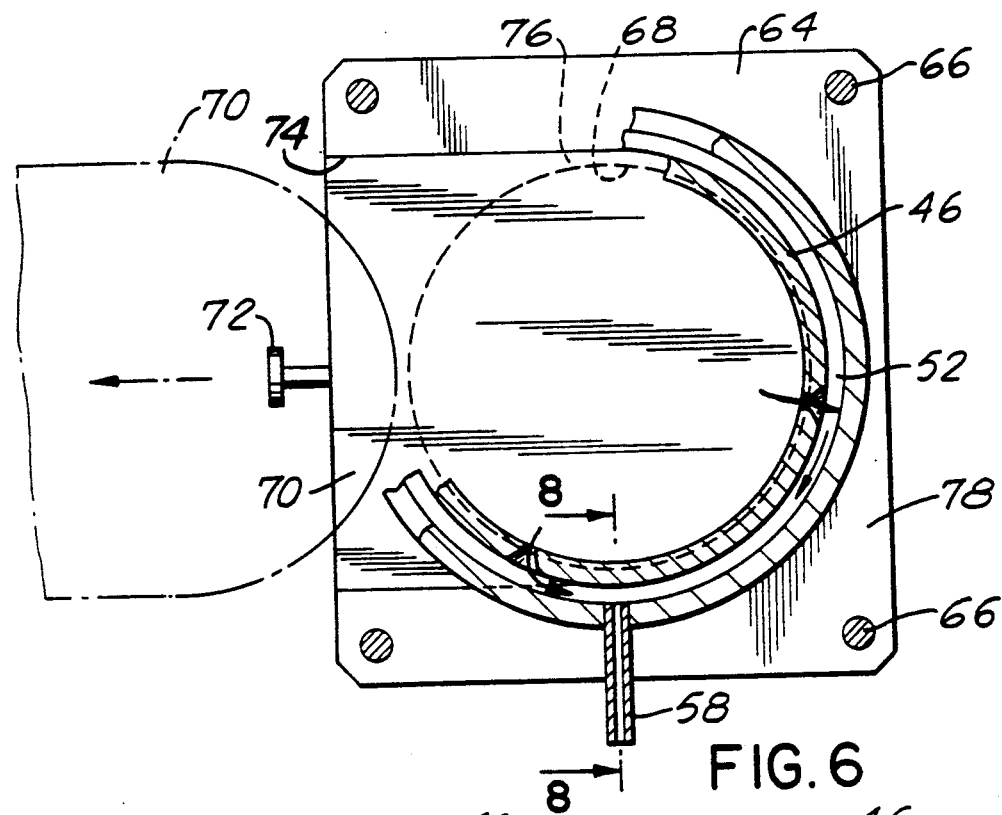
FIG. 6 is a cross-section view of the embodiment of FIG. 5 taken along line 6—6 showing the extension of the drawer to allow waste to be emitted into a containment vessel.
Figure 8:
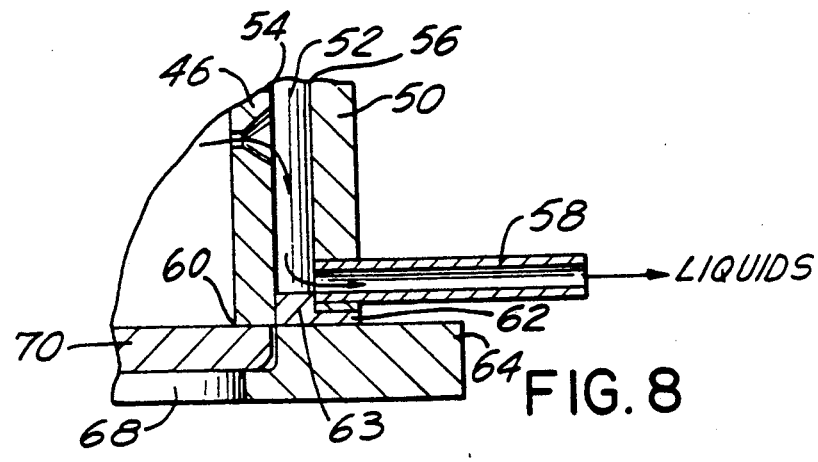
FIG. 8 is a cross-section view taken along line 8—8 of FIG. 6 showing the nozzle and drainage chamber arrangement.

Referring now to FIGS. 5, 6, and 8, the bottom ends 60,62 of the inner and outer chambers 46, 50 are securely affixed flush to a bottom plate 64. The bottom end 60 of the inner chamber 46 is brazed o otherwise attached to a ledge 63 resting upon the bottom plate 64. The bottom end 62 of outer chamber 50 sits on the ledge 63. The bottom plate 64, itself horizontally, affixed to a supporting structure 66 that supports the disposal device 10, has an opening 68 which is substantially coaxial with the interior of the inner chamber 46. Note that the inner and outer chambers 46, 50 are affixed to the bottom plate 64 such that the internal diameters of the chambers 46, 50 exceed the diameter of the opening 68 (the ledge 63 running around the circumference of the opening 68 so as to prevent liquids accumulated within the drainage chamber 52 to escape through the opening 68). Thus, liquids entering the drainage chamber 52 will not be permitted to escape via the opening 68, but rather are collected within the drainage chamber 52 and are removed via the pipe 58 for external collection.

A drawer 70, having a handle 72, is slidably mounted in a recessed portion 74 of the bottom plate 64. The opening 68 of the bottom plate 64 passes through this recessed portion 74, but the recess is wider than the opening 68, so that "rails" 76 are formed along the recessed portion 74, along which rails 76 the drawer 70 slides.

As configured, the drawer 70 forms an integral portion of the bottom plate 64. Advantageously, the planar surface of the drawer 70 is substantially co-planar with and covers the opening 68 of the bottom plate 64.

Figure 7:
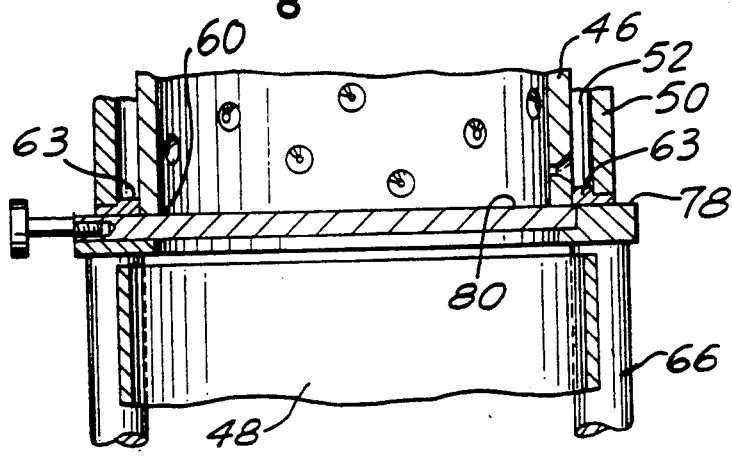
FIG. 7 is a cross-section view of the embodiment of FIG. 5 taken along line 7—7 further showing the construction of the integral drawer in relation to the bottom plate and chambers of the embodiment.

Viewed from FIG. 7, as the drawer 70 may be formed as an integral portion of the bottom plate 64, the top surface 80 of the drawer 70 lies flush with the top surface 78 of the bottom plate 64. Notably, then, the top surface 80 of the drawer 70 also lies flush with the plane formed by the bottom end 60 of the inner chamber 46. Thus, when the drawer is slid into the recess 74, the drawer 70 may serve as a bottom portion for the inner chamber 46, as well as to cover the opening 68 of the bottom plate 64. Waste material introduced into the disposal 10 will thus be compacted against the drawer 70 (see FIG. 9). When the drawer 70 is slid out of the recess 74, the interior of the inner chamber 46 is exposed to the opening 68 of the bottom plate 64, so that compacted waste 82 is allowed to drop into a collection canister 48 located directly below the bottom plate 64.

The collection canister 48, having a closed bottom 84 and sidewalls 86, is substantially hollow and rests on a base plate 88 affixed to the supporting structure 66. The canister 48 may be physically removed from the disposal 10 via a handle 90, so that the entire canister 48 may be autoclaved with the compacted waste 82 therein.

Figure 9:
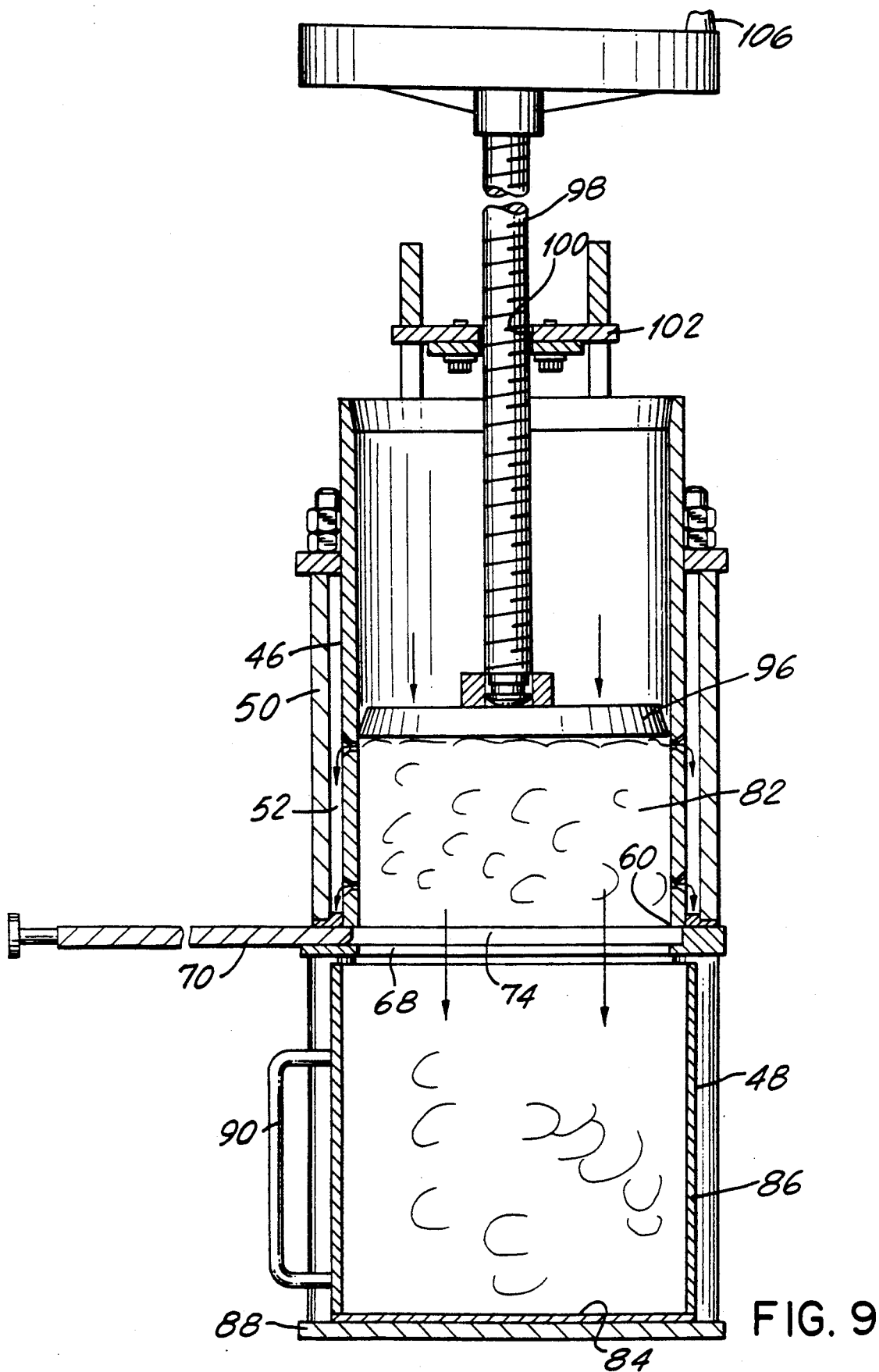
FIG. 9 illustrates operation of the embodiment of FIG. 5

Referring to FIGS. 5, 5(a), and 9, a plunger mechanism 92 is pivotely affixed to a top plate 94 attached to the supporting structure 66. The plunger mechanism 92 comprises, for example, a flat or planar plunger portion 96 substantially conforming to the interior dimensions of the inner chamber 46. The plunger portion 96 is affixed to a threaded rod 98 at one end, which rod 98 passes through a threaded opening 100 in a support plate 102. The support plate 102 is horizontally affixed to U-shaped bridge plates 104. A handle 106, affixed at the other end of the rod 98, serves to rotate the rod 98 through the threaded opening 100.

Two pairs of pivot plates 108, having openings 110, are vertically attached to the top plate 94. The U-shaped bridge plates 104 also have openings 112 formed at the ends 114. The ends 114 are placed within the spaces 116 defined between each pair of pivot plates 108, so that the openings 110 of the pivot plates 108 and openings 112 of the U-shaped bridge plates 104 are substantially coaxial. Removable pivot pins 118 pass through these co-axial openings so that when both pins 118 are in place, the bridge plates 104 are pivotally secured horizontally across the top plate 94.

In operation, a user rotates the handle 106, either clockwise or counterclockwise, to either insert or retract the plunger portion 96 into or out of the inner chamber 46 of the disposal 10. The plunger portion 96 will compact waste material 82 against the drawer 70 of the disposal 10.

Advantageously, the plunger mechanism 92 may be pivotedly displaced on either side of the disposal 10, for easy access to the interior of the disposal 10. This is accomplished by removing one of the pivot pins 118 from either of the pairs of pivot plates 108, thereby allowing the U-shaped brackets 104 to pivot about the other set of pivot plates 108 via the still affixed pivot pin 118 (the plunger portion 96 being retracted from the interior of the inner chamber 46). Alternatively, both pivot pins 118 may be removed, so that the plunger mechanism 92, with its U-shaped bridge plates 104, may be completely removed from the device 10. This is desirable, for example, for the cleaning or maintenance of the disposal 10 or of the plunger mechanism 92.

Still other embodiments will be obvious to a skilled artisan from the method and apparatus taught by the present invention Therefor, as many apparently widely different embodiments of the invention may be made without departing from the spirit and scope therein, it is to be understood that this invention is not to be limited to the specific embodiments shown.

I claim:

1. A method for the disposal of medical waste and separation thereof into liquid and solid components to permit separate autoclave of said liquid and solid components, including the steps of:
   (a) introducing, through an open top end medical waste, containing both liquid and solid components into the interior of a disposal unit having an outer chamber and a perforated inner chamber with said outer chamber to define a drainage chamber between said outer chamber and said perforated inner chamber that extends around the periphery of said perforated inner chamber, said disposal unit further including a slidable drawer slidably positioned flush with the bottom surface of said perforated inner chamber;
   (b) separating the liquid component out of said medical waste by allowing the liquid component to flow through perforations in said perforated inner chamber and into said drainage chamber for collection by an external liquid collector vessel in communication with said drainage chamber;
   (c) compacting the medical waste introduced into the interior of said disposal unit to form a solid compacted medical waste component;
   (d) ejecting the solid compacted medical waste component by horizontally sliding said slidable drawer to allow the solid compacted medical waste component to drop into a separate collection vessel.

2. The method according to claim 1, wherein said waste compacting step further comprises:
   rotating a horizontal support plate into position across the open top end of said disposal unit after the medical waste has been introduced into said disposal unit;
   firmly securing the horizontal support plate across the open top open end of said disposal unit with pivot pins that are slidably inserted to connect bridge plates that are attached to said horizontal support plate to vertical support plates that are attached to said disposal unit; and
   rotating a handle connected to the top end of a threaded rod threadably inserted through the horizontal support plate to lower a planar plunger connected to the bottom end of the threaded rod so that the plunger compacts the medical waste against the slidable drawer.

3. A waste disposal method according to claim 1, wherein said compacting step may be repeated many times prior to being completed.

4. A waste disposal method according to claim 1, further including the step of allowing said liquids in said liquid collector to drain into a second container to be autoclaved.

5. A waste disposal method according to claim 1, further including the steps of removing said liquid collector, and separately autoclaving said collector with said liquids contained therein.

6. A disposal unit apparatus for the disposal of medical waste and separation thereof into solid and liquid components for separate autoclaving of solid and liquid components, said apparatus comprising:
 (a) a disposal unit having an outer chamber and a perforated inner chamber placed with said outer chamber to define a drainage chamber between said outer chamber and said perforated inner chamber that extends around the periphery of said perforated inner chamber;
 (b) a slidable drawer slidably positioned flush with the bottom surface of said perforated inner chamber;
 (c) an external liquid collector vessel in communication with said drainage chamber;
 (d) compactor means for compacting medical waste introduced into the interior of the disposal unit; and
 (e) a solid collector vessel for collecting solid medical waste material upon the sliding of said slidable drawer.

7. A disposal unit according to claim 6 wherein the compactor means is a compactor pivotally affixed at opposite ends at the tope of the disposal unit.

8. An apparatus for the disposal of medical waste, and separation thereof into solid and liquid components for separate autoclaving of solid and liquid components comprising:
 (a) an outer chamber, said outer chamber having an outer surface, an inner surface, an open top end, an open bottom end, and a hollowed interior;
 (b) a perforated inner chamber, said perforated inner chamber having an outer surface, an inner surface, an open top end, an open bottom end, and a hollowed interior, said perforated inner chamber placed within the hollowed interior of said outer chamber such that a space is created between the outer surface of said perforated inner chamber and the inner surface of said outer chamber, said space which defines a drainage chamber around the periphery of said perforated inner chamber;
 (c) a supporting structure for supporting said outer chamber and perforated inner chamber;
 (d) a bottom plate horizontally affixed to said supporting structure, for supporting the open bottom ends of said outer chamber and said perforated inner chamber, said bottom plate having a recessed portion with an opening therethrough substantially coaxial with the hollowed interior of said perforated inner chamber;
 (e) a drawer slidably positioned within and substantially conforming to the dimensions of said recessed portion of said bottom plate, said drawer dimensioned to cover said opening when said drawer is slid within said recessed portion, said drawer having a top surface substantially flush with the top surface of said bottom plate;
 (f) a top plate horizontally affixed to said supporting structure; and
 (g) compaction means for compacting medical waste contained within said perforated inner chamber against said drawer, said compaction means pivotally affixed to said top plate.

9. The apparatus according to claim 8, further comprising draining means in communication with said drainage chamber for draining liquids from said apparatus to an external collector vessel.

10. The apparatus according to claim 8, further comprising a hollow canister removably placed beneath said bottom plate for catching compacted waste released through the opening of said bottom plate.

11. The apparatus according to claim 8, wherein said compaction means comprises:
 (a) a horizontal support plate having a threaded opening;
 (b) a pair of U-shaped bridge plates affixed to said support plate, said bridge plates having free ends with smooth openings therethrough;
 (c) vertical support plates for engaging said bridge plates, said support plates having smooth openings substantially coaxial with the openings of the free ends of said bridge plates;
 (d) pivot pins for horizontally supporting said bridge plates across said vertical support plates, said pins removably inserted through the coaxial openings of said vertical support plates and said bridge plates;
 (e) a threaded rod having a top end and bottom end, said threaded rod passing through said threaded opening of said horizontal support plate;
 (f) plunger means secured to the bottom end of said threaded rod, said plunger means retractably inserted into and substantially conforming to the dimensions of the hollowed interior of said perforated inner chamber; and
 (g) a handle affixed to the top end of said threaded rod for rotatably retracting said plunger means into and out of said perforated inner chamber.

* * * * *